United States Patent [19]

Fujiwhara et al.

[11] 3,961,959

[45] June 8, 1976

[54] PROCESS FOR DEVELOPING A LIGHT-SENSITIVE SILVER HALIDE PHOTOGRAPHIC MATERIAL

[75] Inventors: Mitsuto Fujiwhara; Keiji Kasai; Yoshinobu Nakagawa; Hiroshi Tokura; Kenji Itoh; Seiji Muramoto, all of Hino, Japan

[73] Assignee: Konishiroku Photo Industry Co., Ltd., Tokyo, Japan

[22] Filed: Jan. 28, 1974

[21] Appl. No.: 436,868

[30] Foreign Application Priority Data

Feb. 5, 1973 Japan.............................. 48-13811

[52] U.S. Cl...................................... 96/66.3; 96/3; 96/95
[51] Int. Cl.$^2$ ...................... G03C 5/30; G03C 7/00; G03C 1/06
[58] Field of Search ............. 96/100, 3, 29 D, 66.3, 96/95

[56] References Cited
UNITED STATES PATENTS

| | | | |
|---|---|---|---|
| 3,227,551 | 1/1966 | Barr et al................................. | 96/3 |
| 3,620,745 | 11/1971 | Seymour................................ | 96/100 |
| 3,632,345 | 1/1972 | Marx...................................... | 96/95 |
| 3,674,478 | 7/1972 | Grasshoff et al....................... | 96/3 |
| 3,703,375 | 11/1972 | Groet et al............................. | 96/100 |
| 3,859,095 | 1/1975 | Morcher et al. ....................... | 96/9 |
| 3,869,291 | 3/1975 | Mader et al. .......................... | 96/9 |

*Primary Examiner*—Mary F. Kelley
*Attorney, Agent, or Firm*—Flynn & Frishauf

[57] ABSTRACT

A process for developing a light-sensitive silver halide photographic material in the presence of a new development inhibitor releasing type compound which liberates a compound having development inhibiting action and simultaneously produces a colourless compound.

21 Claims, No Drawings

PROCESS FOR DEVELOPING A LIGHT-SENSITIVE SILVER HALIDE PHOTOGRAPHIC MATERIAL

This invention relates to a process for developing a light-sensitive photographic material in the presence of a new development inhibitor releasing type compound.

Heretofore, it is well known that compounds releasing development inhibitors (hereinafter referred to as Development Inhibitor Releasing type compounds) are incorporated in advance into a light-sensitive photographic material depending upon density of images. These compounds are generally of the type of compounds which react with the oxydation products of the colour developing principal agents and liberate development inhibitors. Typically are known so-called DIR-couplers in which radicals forming the compounds having development inhibiting action are introduced in the active positions of couplers when the couplers are eliminated from the active positions of the couplers. These couplers themselves form dyes on coupling reaction with oxydation products of colour developing principal agents and simultaneously liberate development inhibitors.

The development inhibitor releasing type compounds are generally used for the following purposes. That is, the development inhibitor releasing type compounds are characterized by liberating development inhibitor corresponding to the density of the images and the released development inhibitors inhibit the development corresponding to the image density when the layer is emulsion layer. Accordingly, they expect to achieve two image effect: so-called intra-image effects such as the image tone control, fine graininess and sharpness of images and the inter-image effects such as masking to inhibit the development of the other layer into which the said development inhibitor diffuses in light sensitive materials for colour photography, the said inhibition being corresponding to the image density of the layer from which diffused inhibitors originate, and improved colour caused by inhibiting the development of other layers in the case of single colour light exposure.

Although various types of such development inhibitor releasing type compounds are heretofore known, they have proven unsatisfactory for the above mentioned purposes. For instance, a careful selection of colour is necessary so as to prevent turbid images or to obtain preferred inhibiting effects because the development inhibitor releasing type compounds form dyes in colour development. They were sometimes found to be utterly unsuitable for some types of light-sensitive to photographic materials. Other defects are such that the non-dye forming compounds must be added in a great amount because of its inferior reactivity with the oxydation compounds which are used as colour developing principal agents, and this addition deteriorates specified character (such as sensitivity) and durability.

The present invention obviates such defects as above mentioned and imparts excellent properties to the image obtained by the excellent intra-images and inter-image through the use of a certain type of compounds as the development inhibitor releasing type compounds.

The development inhibitor releasing type compounds used in the present invention are those which release the development inhibitors by the reaction with oxydation products of colour developing principal agents and at the same time form colourless compounds and have the following general formula:

general formula:

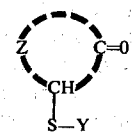

wherein Z represents a radical of non-metallic atoms required to form a heterocyclic ring and Y represents a radical capable of forming a compound having development inhibiting action together with a sulphur atom when the sulphur atom of thioether bond is split from the heterocyclic ring. Since these compounds substantially form colourless compounds when they react with oxydation products of colour developing principal agents and these formed compounds do not constitute a part of the final images, it is not, necessary to use different compounds for different purposes, i.e. types of layers. Thus, a single compound may advantageously be used for all layers and for all the types of photographic materials. Because of extremely good reaction with oxydation products of colour developing principal agents, it is possible to obtain excellent intra- and inter-images with small addition thereof. In the compound of the above general formula, selection from diffusion type and non-diffusion type development inhibitor releasing type compounds is available depending on the types of heterocyclic rings or the substituents thereof, thus offering advantages of selection for purposes. For example, it is possible to incorporate the diffusion type compounds into an arbitrary layer constituting the light sensitive colour photographic materials. In an extreme case, it is possible to cause them to react with the whole layers by addition of them to only one layer. The diffusion type compounds may further be contained in the colour developer. On the other hand, the nondiffusion type compounds are particularly useful when imparting intra- and inter-image effects to a specific layer, or for example when varying the densities between the layers so as to give a certain tone thereto.

Representative examples of compounds having the above general formula are such that Z in the formula represents a heterocyclic ring radical including nitrogen, oxygen or sulphur atoms in one of 5 – 7 membered ring; the representative heterocyclic rings are piperidones, (for example, 2-piperidone, 3-piperidone and 4-piperidone), lactones (for example, lactones of 4 – 7 membered ring), lactams (for example, piperidone), hydantoin, indole (for example, oxyindole), and including those that have more than one substituents such as alkyl, aryl, alkoxy, arylhydroxy, and acyl radicals, halogen atoms and water soluble radicals (such as carboxylic acid, sulfonic acid) or those which form a condensed ring at a suitable position (such as condensed with heterocyclic or aromatic ring).

These heterocyclic rings may have more than one -SY (Y is the same as above) at the carbon atom next to the carbonyl radical. On the other hand, Y in the formula is a radical to form such compound having development inhibiting action together with a sulphur atom as an aryl mercapto-compound, a heterocyclic mercapto-compound, thioglycol type compound, cysteine or glutathione when the sulphur atom of thioether bond is splitted.

For example, the representative mercapto-compounds are heterocyclic mercapto-compounds such as mercaptotetrazole compounds, especially, 1-phenyl-2-mercaptotetrazole, 1-nitrophenyl-5-mercaptotetrazole, 1-naphthyl-5-mercaptotetrazole and the like, mercaptothiazole compounds, especially, 2-mercaptobenzthiazole, mercaptonaphthothiazole and the like, mercaptooxydiazole compounds, mercaptopiperidine compounds, mercaptothiadiazole compounds, especially, 2-mercaptothiadiazolotriazine compound or mercaptotriazine compounds, mercaptotriazole compounds, or mercaptobenzene compounds, especially, 1-mercapto-2-benzoic acid, 1-mercapto-2-nitrobenzene, 1-mercapto-3-heptadecanoylaminobenzene.

The representative examples of these compounds having the above formula are as follows:

(1)
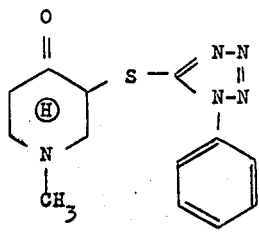

(2)
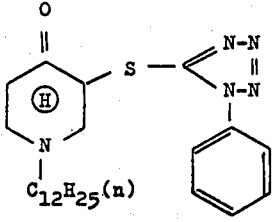

(3)
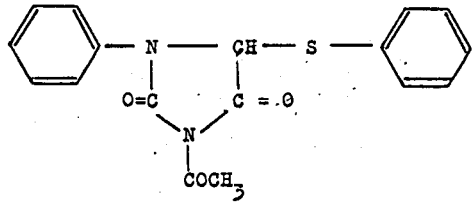

(4)
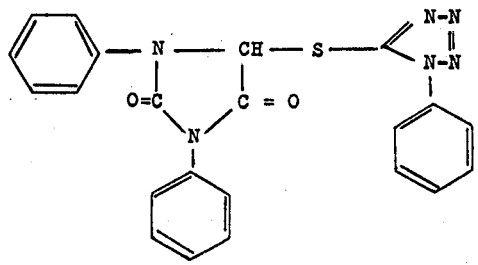

(5)
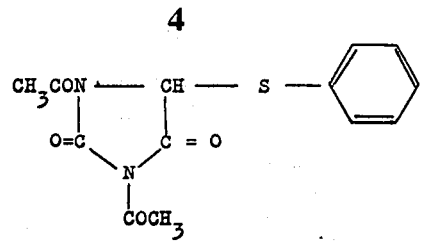

(6)
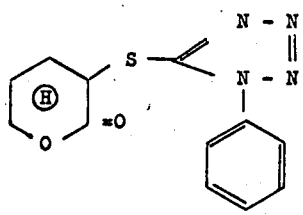

(7)
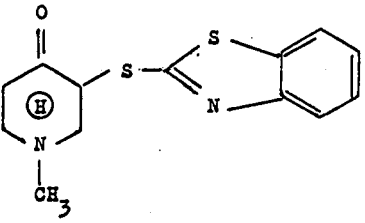

(8)
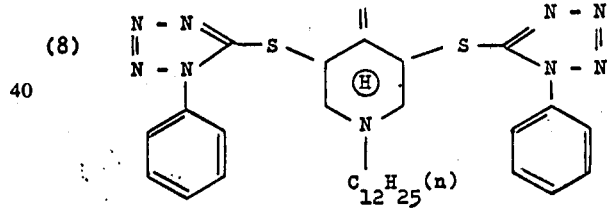

(9)
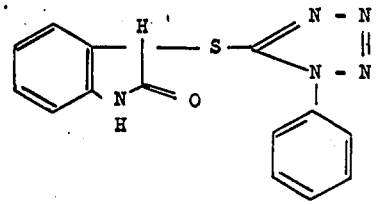

(10)
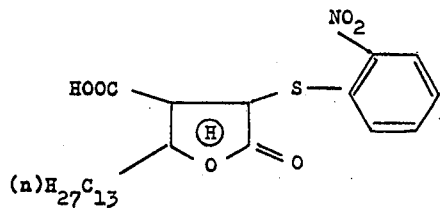

(11)

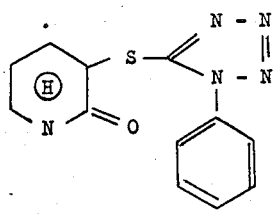

(12)

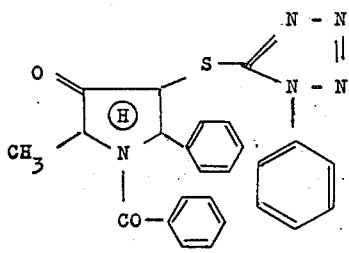

(13)

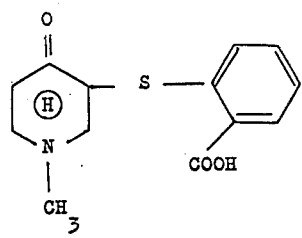

Further there is a compound, for example, which has the following formula which is included in the above general formula, but is not included in the compounds group which forms substantially colourless compound because of reacting with the oxidation products of colour developing principal agents to form a coloured compound.

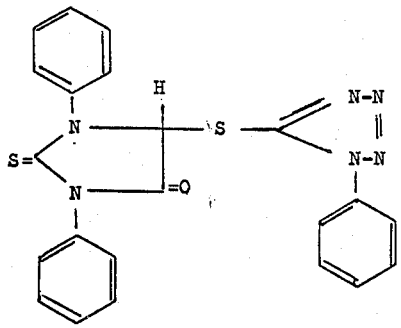

The synthesis methods of the representative compounds according to this invention will be exemplified below, but other compounds can be synthesized based on these synthesis methods.

Synthesis example (1)

Synthesis of exemplified compound (1)

To purified chloroform 14.9 g of N-methyl-4-piperidone hydrochloride was dissolved and to this solution a purified chloroform solution of 21.2 g of 1-phenyl-5-tetrazolylsulfenylchloride was added at 18° – 20°C. This reaction solution was concentrated and 100 ml of benzene was added thereto to produce pale yellow precipitate. After filtration, this precipitate was recrystallized from carbon tetrachloride to give the object compound having m.p. 118° – 120°C.

Synthesis example (2)

Synthesis of exemplified compound (9)

To purified chloroform 6.1 g (2/100 mol.) of N-dodecyl-4-piperidone hydrochloride was dissolved and a chloroform solution of 8.5 g (4/100 mol.) of 1-phenyl-5-tetrazolylsulfenylchloride was added dropwise to this solution with stirring at 18° – 20°C. After stirring for 30 minutes, the chloroform was distilled off under reduced pressure and 150 ml of benzene was added to the residue to form a precipitate which was subsequently filtered off. The precipitate was washed with cooled chloroform to give white crystalline object compound having m.p. 45° ~ 46°C.

Synthesis example (3)

Synthesis of exemplified compound (4)

To purified chloroform 2.5 g (1/100 mol.) of 1,3-diphenylhydantoin was dissolved and sulfurylchloride was added dropwise to this solution at 0° – 5°C and the solution was stirred for 30 minutes. The chloroform was distilled off under reduced pressure at a temperature of less than 10°C and this residue was dissolved in 50 cc of acetone. To the solution 2.0 g (1/100 mol.) of 1-phenyl-5-mercaptotrazole sodium salt was added and refluxed for 30 minutes. The formed sodium chloride was filtered off and the filtrate was concentrated under reduced pressure. The formed crystals were recrystallized from methanol to give the object compound having m.p. 108° – 113°C.

The compounds having the above general formula can be synthesized according to these synthesis examples. Exemplary analyses of exemplified compounds (1) – (13) thus obtained are shown below.

| Exemplified compound | Molecular formula | Elementary analyses (C, N, H, S) | | |
|---|---|---|---|---|
| | | | Calcd. (%) | Found (%) |
| (1) | $C_{13}H_{15}N_5OS$ | C | 53.96 | 53.78 |
| | | H | 5.23 | 5.05 |
| | | N | 24.21 | 24.04 |
| | | S | 11.08 | 11.06 |
| (2) | $C_{24}H_{37}N_5OS$ | C | 64.97 | 65.01 |
| | | H | 8.41 | 8.07 |
| | | N | 15.79 | 15.66 |
| | | S | 7.23 | 7.09 |
| (3) | $C_{17}H_{14}N_2O_3S$ | C | 62.56 | 62.39 |
| | | H | 4.32 | 4.30 |
| | | N | 8.59 | 5.55 |
| | | S | 9.83 | 9.78 |
| (4) | $C_{22}H_{16}N_6O_2S$ | C | 61.67 | 61.49 |
| | | H | 3.76 | 3.81 |
| | | N | 19.62 | 20.02 |
| | | S | 7.48 | 7.57 |
| (5) | $C_{13}H_{13}N_2O_4S$ | C | 53.23 | 53.08 |
| | | H | 4.47 | 4.56 |
| | | N | 9.55 | 9.71 |
| | | S | 10.93 | 11.10 |
| (6) | $C_{12}H_{12}N_4O_2S$ | C | 52.16 | 51.95 |
| | | H | 4.38 | 4.27 |
| | | N | 20.28 | 20.54 |

-continued

| Exemplified compound | Molecular formula | Elementary analyses (C, N, H, S) Calcd. (%) | Found (%) |
|---|---|---|---|
| (7) | $C_{13}H_{14}N_2OS_2$ | S 11.61 | 11.60 |
| | | C 56.08 | 56.31 |
| | | H 5.07 | 5.16 |
| | | N 10.07 | 10.11 |
| (8) | $C_{31}H_{41}N_9OS_2$ | S 23.04 | 23.30 |
| | | C 60.07 | 59.88 |
| | | H 6.67 | 6.44 |
| | | N 20.34 | 20.21 |
| (9) | $C_{15}H_{11}N_5OS$ | S 10.35 | 10.13 |
| | | C 58.24 | 58.53 |
| | | H 3.59 | 3.91 |
| | | N 22.64 | 23.01 |
| (10) | $C_{25}H_{36}N_4O_4S$ | S 10.37 | 9.97 |
| | | C 61.45 | 61.80 |
| | | H 7.43 | 7.66 |
| | | N 11.47 | 11.15 |
| (11) | $C_{12}H_{13}N_5OS$ | S 6.56 | 6.29 |
| | | C 52.35 | 52.04 |
| | | H 4.76 | 4.68 |
| | | N 25.44 | 26.01 |
| (12) | $C_{25}H_{21}N_5O_2S$ | S 11.65 | 11.95 |
| | | C 65.91 | 65.94 |
| | | H 4.65 | 4.73 |
| | | N 15.38 | 15.26 |
| (13) | $C_{13}H_{15}NO_3S$ | S 7.04 | 7.02 |
| | | C 58.84 | 59.00 |
| | | H 5.70 | 5.84 |
| | | N 5.28 | 5.19 |
| | | S 12.09 | 11.88 |

Compounds thus synthesized represented by the said formula may be used for various light-sensitive silver halide photographic materials such as for black-and-white, colour and pseudo-colour photography as well as for general black-and-white, printing black-and-white purposes, X ray, electron rays, high resolving power black-and-white, general colour, colour X-ray, diffusion-transfer type colour, dye breech colour, etc. Silver halide used therein are silver chloride, silver bromide, silver iodide, mixed silver halide (such as silver chlorobromide, silver iodobromide, silver chloro-iodobromide and the like), and may be manufactured by such methods as with conversion-emulsion, Lippmann emulsion according to the type of light-sensitive photographic materials. The granularity diameter, the amount contained and the mixed ratio of silver halides vary depending on the type of the photographic materials used. Generally, the type with comparatively lower sensitivity, fine particles mainly used silver chloride while that with higher sensitivity would contain less silver chloride. This type of silver halide which is of direct reversal type is imparted with optical or chemical fog. These silver halides may be sensitized with gelatine, sulphur sensitization agent such as allylthiocarbamide, thiourea, cystine, selenium sensitization agent, noble metal sensitization agent such as gold sensitization agent, and more concretely potassium chloroaurite, potassium auriocyanate, potassium chloroaurate, 2-aurosulfobenzothiazol methochloride or the sensitization agents of ruthenium, rhodium, palladium, iridium salt which are more concretely ammonium chloropaladate, potassium chloroplatinate and sodium chloropaladide. They are known to act as sensitization agents or fog inhibitors depending upon the amount and they may be used singly or in combination to enhance chemical sensitivity.

These silver halides may be directly placed in a layer by vacuum evaporation, etc. to a support without any binders or placed in a layer on a support with which is diffused into a so-called silver halide emulsion type binder comprising of one or two of gelatine or other colloidal substances such as colloidal alubumin cellulose derivatives or synthetic resins such as polyvinyl compounds and provided in a layer on the support via an under layer, intermediate layer, etc. The said silver halide emulsion may be optically sensitized by, for instance, a cyanine dye, merocyanine dye. In light-sensitive colour photographic materials, three types of silver halide emulsions with different sensitivity wave ranges are used. The said emulsion may be stabilized by triazole compounds, azaindene compounds, quaternary benzothiazolium compounds and zinc or cadmium compounds, and may contain sensitization compounds of quaternary ammonium salt type or polyethylene glycol type. It may also contain a suitable gelatine plasticizer such as a dihydroxyalkane, for example, glycerine and 1,5-pentanediol, ester of ethylenebisglycolic acid, bisethoxydiethyleneglycol succinate, amides of acrylic acid type compound, latex, etc. and also such additives as the compounds having a halogen-substituted fatty acid, acid anhydride, e.g. formaldehyde, mucobromic acid, dicarboxylic acid chloride, diester of methane sulfonic acid, hardening agent such as sodium bisulfite salt of dialdehyde in which each aldehyde group is separated by two or three carbon atoms, or coating agents such as saponine, or coating assistants such as sulfosuccinic acid.

The light-sensitive colour photographic materials, in particular, contain such couplers as a 5-pyrazolone type magenta coupler, naphthol and phenol type cyane coupler and yellow coupler having an active methylene group between carboxyl groups at the second position and these may either be a molar or four molar coupler, or may contain so-called masking couplers having an arylazo radical at active positions. It is preferable, in this instance, to use a so-called colourless coupler which are colourless before colour development and said masking coupler in combination. When incorporated into an emulsion, the coupler may be added directly to the emulsion or suspended into it using a solvent of coupler.

Also, to promote the photographic characteristics, the so-called combining couplers can be contained therein in combination of several couplers. In light-sensitive colour photographic material for diffusion transfer, dye developing agents or a coupler developing agent can be contained instead of couplers. The dye developing agents are the compounds having both the function of dye and that of development, for example, those in which hydroquinone, aromatic primary amino colour developing agents and the like are introduced, and coupler developing agents are the compounds having both the function of coupler and that of development, for example, those in which hydroquinone and the like are introduced in active positions or in positions other than the active positions of the above couplers or in lightsensitive colour photographic material used for silver dye bleaching method, dye may be incorporated in advance.

And in a light-sensitive colour photographic material, ultraviolet ray absorption agents and fluorescent bleaching agents and the like, if necessary, may be incorporated.

Such silver halide emulsions may be placed on supports, if necessary, through an underlayer and an intermediate layer and thus light-sensitive silver halide photographic materials can be manufactured. As supports in this case, for example, paper, laminate paper, glass and film-sheet of cellulose acetate, cellulose nitrate, polyester, polyamide, polystyrene and the like are used and these supports can be selected dependent upon the object of use of light-sensitive photographic material. In principle, the light-sensitve photographic material is composed of a support and a sensitive layer (silver halide vacuum evaporation layer or emulsion layer) and dependent upon the kind of light-sensitive photographic material, it may be composed of a multilayer in adequate combination of underlayer, intermediate layer, filter layer, curl-inhibiting layer and protective layer and the like. Also, the sensitive layer itself may be composed of a multilayer consisting of, for example, a layer containing highly sensitive material and a layer containing cooperatively lower sensitive material in the same or different wave-length region. Each of these layers can contain several additive agents, for example, photographic additive agents to be incorporated in the above emulsions and different agents dependent upon the object of each layer, for example, dye for filter in the filter layers and membrane physical character improving agents and antistatic agents in the protective layers. For example, in light-sensitive photographic materials for diffusion transfer, an intermediate layer containing physical developing nuclei may be provided as an embodiment.

Such silver halide light-sensitive photographic materials have excellent photographic characteristics as above mentioned by developing them in the presence of a compound used in this invention having the above general formula. But as an embodiment of this invention there is a method in which the said compounds may be incorporated in light-sensitive photographic materials and developed. In this case, said compounds having diffusive character can be incorporated in each constitutional layer, for example, in one or more than one layer of emulsion layer, intermediate layer, said protective layer and said compounds having non-diffusive character can be preferably incorporated in an emulsion layer or one or more than one layer adjacent to an emulsion layer.

In case said compounds are caused to be incorporated into an light-sensitive photographic material, they may be incorporated into a coating solution of constitutional layer in several types, for example, when diffusive, they can be incorporated by adding in a form of solution and when non-diffusive, they can be incorporated by adding in a form of emulsion. For example, when diffusive, they can be incorporated in a form of alkaline solution and when non-diffusive, they can be incorporated in a form of emulsion dissolved in a solvent of the said couplers. As solvents of said couplers, a high boiling organic solvent immiscible with water such as di-n-butyl phthalate, benzyl phthalate, triphenyl phosphite, tri-o-cresyl phosphate, monophenyl di-p-t-butylphenyl phosphite and the like or lower boiling organic solvents miscible with water such as methyl isobutyl ketone, β-ethoxyethyl acetate, methoxytriglycol acetate, acetone, methyl acetone, methanol, ethanol, acetonitrile, dioxane, dimethyl formamide, ethyl acetate, isopropyl acetate, chloroform and the like may be used and these lower boiling organic solvents may be used instead of high boiling organic solvents and these organic solvents can be used alone or in combination with more than two.

Also, according to a further embodiment of this invention, for example, when another photographic material such as a light-sensitive photographic material for different transfer, for example, a receiving material is used and this receiving material is developed in contact with a light-sensitive photographic material, the compounds having the above general formula according to this invention may be incorporated into other light-sensitive photographic material and at this time the said compounds are preferably those which are generally diffusive, but in cases where, for example, the above receiving material is of the type in which silver halide particles having physical developing nuclei may be incorporated into a receiving layer (for example, gelatine layer, polyvinyl compound layer and the like) on a support, the said compound may be desirably nondiffusive.

According to another embodiment of this invention, in cases where the compounds having the above general formula may be incorporated into other photographic material such as a light-sensitive photographic material or a receiving material, the said compounds can be kept on protecting them until necessary in a specific layer with a carrier such as mordant dependent upon kinds of substituents of the said compounds and, for example, the compounds having anion radicals can be protected by an amino radical and the like in a mordant and when developed, they can be placed in a free state.

Further, according to a still further embodiment of this invention, the said compounds may be incorporated into a developer or in a pre-treatment bath. As developer thus used or pre-treatment baths, for example, a black-and-white developer, colour developer, for example, a colour developer for photographic material including coupler (Ekta type) or for non coupler photographic material (Kodachrome type) and in reversal development, either one or both of the primary and secondary developer and various developers such as a general black-and-white developer, developer for X-ray or pre-treatment bath such as pre-hardening bath may be cited, and the said compounds which may be incorporated in these solutions are desirably diffusive and in this case it is possible to incorporate in advance the carrier into a specific layer of light-sensitive photographic material and emphasize the affect of the specific layer. In these cases, it is desirable that aromatic primary amino colour developing principal agents are present together.

According to this invention, various embodiments as above mentioned are practised, but in every case an excellent image-effect can be obtained in comparison with development inhibitor releasing type compounds in the prior art, and in an embodiment in which the compounds of this invention are incorporated into light-sensitive photographic materials, its image-effect is remarkable. An amount used for the said compounds quite differently vary with the method and object to be applied and the effect to be expected, but 0.1 – 10 g of these compounds per 1 kg of emulsion is desirable. When the same amount of these compounds as that of development inhibitor releasing type compounds in the prior art is used, its image-effect is remarkably great as compared with the prior image-effect and when it is expected that its image-effect is the same amount as the prior image-effect, the amount used for these compounds may be extremely small.

As a composition of an embodiment in which these compounds are incorporated into a treatment solution, for example, a developer, the composition of colour developer for non-coupler photographic material is, for example, as follows:

| | |
|---|---|
| Colour developing principal agent | 2–8 g |
| Sodium sulfite (anhydrous) | 1.0–6 g |
| Sodium carbonate (monohydrated water) | 40–100 g |
| Potassium bromide | 0.5–2 g |
| Coupler | 0.002–0.01 molar amount |
| Compound having the said general formula to be used in this invention | 1.0 g – 5.0 g |
| Add water | to 1l |

As a composition of colour developer solution for Ekta type, the composition in which the coupler is eliminated from the above composition is a representative composition and according to the respective object, the value of pH may be adjusted and further other photographic additive agents may be added thereto.

Further, as a composition of colour developer for Kodachrome type, the following example:

| | |
|---|---|
| N-Ethyl-N-$\beta$-methanesulfonamidoethyl-3-methyl-4-aminoaniline | 5.0 g |
| Sodium sulfite | 2.0 g |
| Benzylalcohol | 3.5 ml |
| Sodium carbonate | 8.2 g |
| Potassium bromide | 1.0 g |
| Coupler | 0.005 mol. |
| Compound having the said general formula to be used in this invention | 2.0 g |
| Add water | to 1l | and as colour developer for Ekta type, the following composition:

| | |
|---|---|
| N-Ethyl-N-$\beta$-methanesulfonamidoethyl-3-methyl-4-aminoaniline sulfate | 5.0 g |
| Sodium sulfite (anhydrous) | 2.0 g |
| Benzylalcohol | 3.8 g |
| Sodium carbonate (1 hydrated water) | 50 g |
| Potassium bromide | 1.0 g |
| Potassium hydroxide | 0.55 g |
| Compound having the said general formula to be used in this invention | 2.5 g |
| Add water | to 1l, | are representatives.

The colour developing principal agents according to this invention are preferably aromatic primary amine compounds, especially those of p-phenylenediamine type such as N,N-diethyl-p-phenylenediamine, N-ethyl-N-$\omega$sulfobutyl-p-phenylenediamine, 2-amino-5-diethylaminotoluene, p-amino-N-ethyl-N-$\beta$-hydroxyethylaniline and the like. It is desirable that the said compounds are present together with one or more than one of these colour developing principal agents when the light-sensitive photographic material is processed to development and the said compound may be used in combination with them and further in combination of the methods according to this invention. For example, as a representative example, there is a method in which a non-diffusive developing inhibitor releasing type compound is caused to be incorporated into a specific layer of light-sensitive photographic material and a diffusive developing inhibitor releasing type compound is caused to be incorporated into a treatment solution and the said light-sensitive material is processed with the said treatment solution.

Thus, after development the light-sensitive photographic material processed by a developing process according to this invention may be subjected to a conventional photographic processing, for example, by a process selected from the process consisting of a stop bath containing an organic acid, a stopping fixer solution containing an organic acid and sodium thiosulfate or ammonium thiosulfate, a fixer solution containing a fixing component such as sodium thiosulfate or ammonium thiosulfate, a bleaching solution containing as a principal component a ferric salt of aminopolycarboxylic acid an alkali halide, a bleaching fixer solution containing fixing components such as a ferric salt of aminopolycarboxylic acid and sodium thiosuflate or ammonium thiosulfate, and other stabilizing solutions, water washings, drying and the like in combination of an adequate process to the light-sensitive photographic material used.

The following examples are given to further illustrate the present invention, but these do not mean that the scope of the invention is to be limited by them.

EXAMPLE (1)

Samples I and II are prepared as follows.

Sample I

In 40 ml of ethyl acetate and 20 g of di-n-butyl phthalate 2.9 g of the exemplified compound (1) and 20 g of 1-hydroxy-N-[$\omega$-(2,4-di-tert-amylphenoxy)-butyl]-2-naphthoamide as cyancoupler were dissolved and this solution was mixed with 20 ml of a 10% solution of Alkanol B (alkyl naphthalenesulfonate, manufactured by Du Pont (E. I.) de Nemours & Co.) and 300 ml of a 50% aqueous gelatine solution and emulsified and dispersed with a colloid mill. After this, the dispersion solution was added to 1 kg of red-sensitive silver iodobromide emulsion and dispersed. This solution was coated on a triacetate base and dried.

Sample II

As control sample, another sample was prepared in the same manner except that the exemplified compound (1) is not contained.

These samples I and II after being exposure through a light wedge were developed by the following developer solution and bleaching and fixation were processed by a usual treatment method.

| | |
|---|---|
| N,N-Dimethyl-p-phenylenediamine hydrochloride | 2.0 g |
| Anhydrous sodium sulfite | 2.0 g |
| Sodium carbonate (monohydrated water) | 82.0 g |
| Potassium bromide | 2.0 g |
| Add water | to 1l |

In both samples, images composed of cyano dye formed. The sensitivity in both is the same but the value of $\gamma$ in sample II is 0.8 and that in sample I is 0.5. Further the magenta image in sample II is composed of remarkably finer granularity than in sample I.

EXAMPLE (2)

Samples III and IV were prepared as follows.

Sample III

In 30 ml of ethyl acetate and 15 ml of dibutyl phthalate 3.1 g of the exemplified compound (8) and 15 g of magenta coupler 1-(2,4,6-trichlorophenyl)-5-oxo-3-{3-[$\alpha$-(2,4-di-t-pentylphenyl)acetamido]benzamido } -2-pyrazoline were dissolved and to this solution 20 ml of a 10% aqueous solution of Alkanol B and 200 ml of a 5% aqueous gelatine solution were mixed and the mixture is emulsified and dispersed. To this dispersed solution 1 kg of green-sensitive silver iodobromide emulsion was added and dispersed. This dispersion solution was coated on a triacetate base and dried.

SAMPLE IV

Sample IV was prepared in the same manner except 4.94 g (two times the molar amount of exemplified compound (8) of p-lauroylamido-ω-(1-phenyl-5-tetrazoylthio) acetophenone (control compound) was used in place of the exemplified compound (8) in sample III.

These samples, after being exposed to light through wedge, was treated in the same manner as in example (1). The results are as follows:

|  | Sensitivity | γ |
|---|---|---|
| Sample III | 97 | 0.5 |
| Sample IV | 98 | 0.70 |

Thus the sensitivity is the same in both, but the value of γ of sample III is remarkably reduced in spite of that the amount used of the exemplified compound (8) is half of that in the control compound and these facts shown that sample III has an excellent effect. The compound according to this invention is superior to control compound in graininess and sharpness of magenta images. Further, the control compound is a development inhibitor releasing type compound described in Japanese Pat. Publication No. 22514/1967.

EXAMPLE (3)

Samples V and VI were prepared as follows.

Sample V

In 1 kg of silver iodobromide sensitized in the red region a solution of 12 g of 4,6-dichloro-5-methyl-2-[α-(2,4-di-t-pentylphenoxy)butylamido] phenol is 15 ml of di-n-butyl phthalate and 15 ml of ethyl acetate was dissolved, dispersed and coated on triacetate base. On this red-sensitive emulsion layer a green-sensitive silver halide emulsion containing 2.1 g of the exemplified compound (2) and 20 g of 1-(2,4,6-trichlorophenyl)-5-oxo-3{3-[α-(2,4-di-t-pentylphenoxy) acetoamido]benzamido}-2-pyrazoline was coated.

Sample VI

Sample VI as control sample was prepared in the same manner except that the green-sensitive layer contains only a magenta coupler and does not contain the compound (2) according to this invention.

After these samples V and VI were exposed to light through a wedge with red light and white light, they were developed with the developer used in example (1) and bleached and fixed in a usual manner.

The values of γ in the cyan images obtained by exposure of sample VI with red light and white light were substantially the same, but the value of γ in the cyan image obtained by exposure of sample V with white light was smaller than that obtained by exposure of sample V with red light. This is because the development inhibitor released from compound (2) by exposure of sample V with white light disperses to the red-sensitive layer in the underlayer and inhibits the development of the redsensitive layer and causes a reduction in the value of γ.

EXAMPLE (4)

Silver iodobromide emulsion prepared as follows was coated on a triacetate base.

To 0.8 g of coupler 4-n-octadecyloxyphenylazo-5-oxo-1-phenyl-3-(3,5-disulfobenzamido)-2-pyrazoline in 40 ml of water 5 cc of a 10% sodium hydroxide solution was added with stirring at room temperature.

solution was poured to a mixture of 100 ml of a 10% gelatin solution and 8 cc of 5% Alkanol B at 40°C and further 1 cc of a 7% saponin solution was added thereto and then the value of pH of this solution was adjusted to 6.8 and 8 cc of silver iodobromide emulsion was added with sitrring for two minutes and the emulsion was allowed to stand at 40°C for 30 minutes, filtered and coated on a support.

Then this coated film was exposed to light at a distance of 1.5 m with a 40-watt electric bulb and was caused to form fog. On this emulsion layer with fog was coated the emulsion prepared by the following method.

To a mixture of 0.5 cc of 2,4-di-n-amylphenol and 0.8 cc of dimethylformamide, 0.4 g of the exemplified compound (4) was added and stirred with heating at 80°C until dissolved. To a mixture of 20 cc of a 10% gelatine solution and 2 cc of a 5% Alkanol B solution this solution was added at 40°C. Then this suspension solution was subjected to a colloid mill five times and the remaining dispersion solution was washed with a mixture of 8 cc of water and 2 cc of 7% saponin solution out of the mill. To the combined dispersion solution was added 10 cc of silver chlorobromide emulsion and stirred for two minutes and after allowed to stand at 40°C for 30 minutes, this emulsion was coated on a film. There was obtained the light-sensitive material for diffusion transfer. After exposure to light, this film was caused to contact with a receiving layer coated with a gelatine solution of 0.5 g of cetyltrimethylammonium bromide in 25 cc of a 10% gelatine solution and developed by the following developer solution:

| Sodium carbonate | 20.0 g |
|---|---|
| Sodium hexamethaphosphorate | 2.0 g |
| Benzyl alcohol | 10.0 g |
| 3-Acetoamido-4-amino-N,N-diethylaniline | 2.0 g |
| Add water | to 1l |
| pH | adjusted to 11 |

As development progressed, a development inhibitor was formed on the light exposure region, dispersed into the under emulsion layer with fog and inhibited the development of the corresponding part. Therefore, as the under emulsion layer with fog in nonexposure part was not inhibited to develop, soluble magenta dye was formed by coupling of a developing principal agent with a coupler. This magenta dye was transferred in images to a receiving layer comprising a mordant and formed clear positive magenta images.

EXAMPLE (5)

On a triacetate base were successively coated the coating solutions having the following compositions (the weight shows that per/m³).

1. A red-sensitive silver iodobromide emulsion containing 440 mg of gelatine and 184 mg of silver halide This emulsion contains also 26.3 mg of 1-hydroxy-4'-(4-t-butylphenoxyl)-4-phenylazo-2-naphthoanilide and 32.7 mg of 1-hydroxy-N-(α-2,4-di-t-amlyphenoxy) butyl-2-naphthoamide as coupler and 6.3 mg of the exemplified compound (2) as development inhibitor releasing type compound.

2. A gelatine intermediate layer containing 83 mg of gelatine and 3 mg of dioctylhydroquinone 3. A green-sensitive silver iodobromide emulsion containing 400 mg of gelatine and 243 mg of silver halide This emulsion contains 24.5 mg of 1-(2,4,6-trichlorophenyl)-4-(4'-methoxyphenylazo)-5-oxo-3-{3-[α-(2,4-di-t-pentylphenoxy) acetoamido]benzamido} -2-pyrazoline and 24.3 mg of 1-(2,4,6-trichlorophenyl)-5-oxo-3-{3-(α-(2,4-di-t-pentylphenoxy) acetamido]benzamido}-2-pyrazoline as a coupler, 9.3 mg of the exemplified compound (8) as development releasing type compound and also 3.5 mg of dioctylhydroquinone as contamination inhibiting agent.

4. A gelatine intermediate layer containing 837 mg of gelatine and 3 mg of dioctylhydroquinone 5. A blue-sensitive silver iodobromide emulsion containing 200 mg of gelatine and 62 g of silver halide This emulsion contains 102.5 mg of N-(p-benzoylacetoamidobenzenesulfonyl)-N-(γ-phenylpropyl)-p-toluidine as a coupler and 16 mg of dioctylhyroquinone as a contamination inhibiting agent.

On the other hand, as control sample, the sample which did not contain the exemplified compound (2) in the red-sensitive layer and the exemplified compound (3) in the green-sensitive layer was prepared.

Both samples were exposed through a light wedge and then developed by the following developer solution at 24°C for ten minutes.

| | |
|---|---|
| Anhydrous sodium sulfite | 2.0 g |
| N-Ethyl-N-β-methanesulfoneamidoethyl-3-methyl-4-aminoaniline sulfate | 5.0 g |
| Sodium carbonate | 50.0 g |
| Sodium bromide | 0.9 g |
| Sodium hydroxide | 4.0 g |
| Sodium hexamethaphosphate | 0.5 g |
| Benzyl alcohol | 4.0 ml |
| Add pure water | to 1l |

Bleaching and fixing were carried out in a conventional way.

The results obtained showed that the sample containing the exemplified compounds (2) and (3) is excellent in sharpness and graininess and has a small fog in comparison with the control sample.

EXAMPLE (6)

An available inner type colour photographic film was exposed through a light wedge and then developed by the following colour developer solution at 20°C for 10 minutes. Thereafter the film was bleached, fixed, washed with water, stabilized and dried in a usual manner.

| | |
|---|---|
| Colour developer solution: | |
| N-Ethyl-N-β-methanesulfonamidoethyl-3-methyl-4-aminoaniline sulfate | 5.0 g |
| Sodium sulfite (anhydrous) | 2.0 g |
| Benzyl alcohol | 3.8 g |
| Sodium carbonate (monohydrated water) | 50 g |
| Potassium bromide | 1.0 g |
| Potassium hydroxide | 0.55 g |
| Exemplified compound (13) | 1.5 g |
| Add water | to 1l |

Also the same colour photographic film as control was developed by the same colour developer solution except that exemplified compound (13) was eliminated. The results thus obtained showed that the film developed according to this invention has remarkably better sharpness and graininess and has brightness in colour in comparison with the control sample.

What is claimed is:

1. A process for developing an imagewise exposed light-sensitive silver halide protographic material in the presence of a development releasing inhibitor compound which liberates a development inhibitor and simultaneously produces a colourless compound, said development releasing inhibitor compound comprising

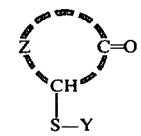

wherein Z represents a group selected from the group consisting of a piperidone, a lactone having a 4- to 7-membered ring, a pyrrolidone, a hydantoin and an oxyindole, and Y represents a group that forms a development inhibitor when the sulphur atom of the thioether bond is split from the heterocyclic ring to release an aryl mercapto compound, a heterocyclic mercapto compound, a thioglycol, cysteine or glutathione.

2. A process for developing a light-sensitive silver halide photographic material as claimed in claim 1 in which Z represents a piperidone derivative radical, lactone derivative radical having 4 – 7 membered ring, pyrrolidone derivative radical, hydantoin derivative radical or oxyindole derivative radical and Y represents a mercaptotetrazole derivative radical, mercaptothiazole derivative radical, mercapto-oxydiazole derivative radical, mercaptopiperidine derivatives radical, mercaptothiadiazole derivative radical, mercaptotriazine derivative radical or mercaptobenzene derivative radical.

3. A process for developing a light-sensitive silver halide photographic material as claimed in claim 1 in which Z represents a radical selected from 2-piperidone, 3-piperidone and 4-piperidone derivative radical, lactone derivative radical having 5 – 6 membered ring, pyrrolidone derivative radical, hydantoin derivative radical and oxyindole derivative radical and Y represents a radical selected from 1-phenyl-2-mercaptotetrazole radical, 1-nitro-phenyl-5-mercaptotetrazole radical, 1-naphthyl-5-mercaptotetrazole radical, 2-mercaptobenzthiazole radical, mercaptonaphthothiazole radical, 2-mercaptothiazole radical, 1-mercapto-2-benzoic acid radical, 1-mercapto-2-nitrobenzene radical and 1-mercapto-3-heptadecanoylaminobenzene radical.

4. A process for developing a light-sensitive silver halide photographic material as claimed in claim 1 in which said compound is used in an amount of 0.1 – 10 g per 1 kg of an emulsion.

5. A process of claim 1 wherein the development releasing inhibitor compound is

6. A process of claim 1 wherein the development releasing inhibitor compound is

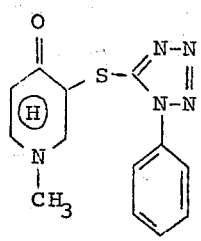

7. A process of claim 1 wherein the development releasing inhibitor compound is

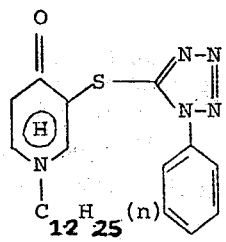

8. A process of claim 1 wherein the development releasing inhibitor compound is

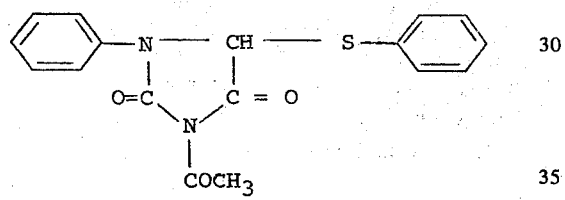

9. A process of claim 1 wherein the development releasing inhibitor compound is

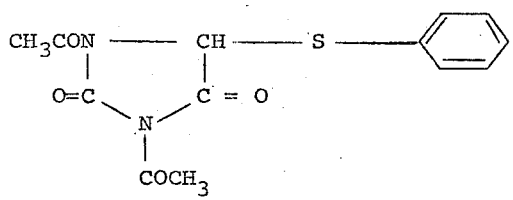

10. A process of claim 1 wherein the development releasing inhibitor compound is

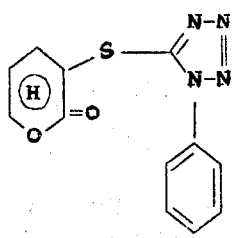

11. A process of claim 1 wherein the development releasing inhibitor compound is

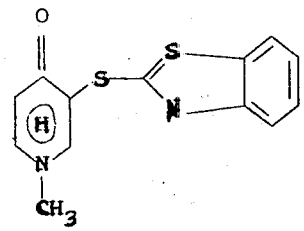

12. A process of claim 1 wherein the development releasing inhibitor compound is

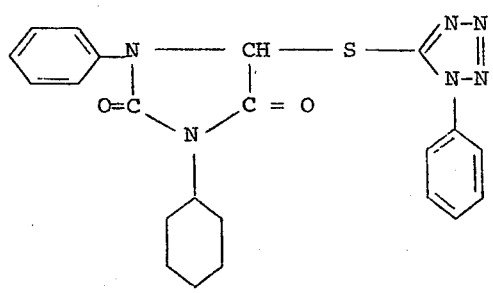

13. A process of claim 1 wherein the development releasing inhibitor compound is

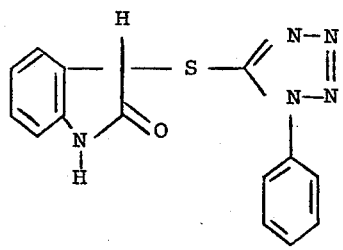

14. A process of claim 1 wherein the development releasing inhibitor compound is

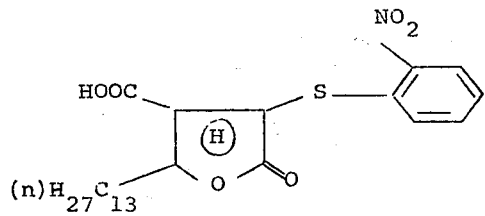

15. A process of claim 1 wherein the development releasing inhibitor compound is

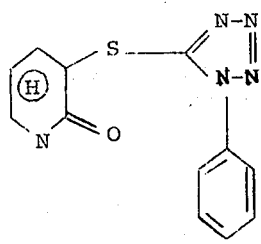

16. A process of claim 1 wherein the development releasing inhibitor compound is

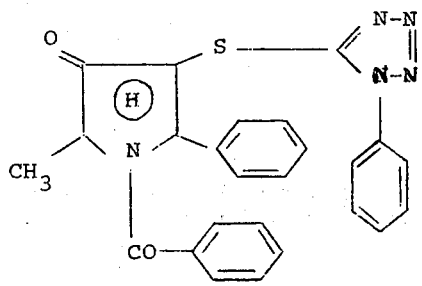

17. A process of claim 1 wherein the development releasing inhibitor compound is

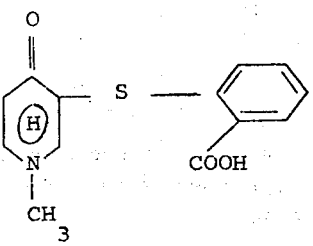

18. A process of claim 1 wherein Y represents a group that forms a development inhibitor when the sulphur atom of the thioether bond is split from the heterocyclic ring to release a heterocyclic mercapto compound.

19. A process of claim 1 wherein Y represents a group that forms a development inhibitor when the sulphur atom of the thioether bond is split from the heterocyclic ring to release a thioglycol.

20. A process of claim 1 wherein Y represents a group that forms a development inhibitor when the sulphur atom of the thioether bond is split from the hterocyclic ring to release cysteine.

21. A process of claim 1 wherein Y represents a group that forms a development inhibitor when the sulphur atom of the thioether bond is split from the heterocyclic ring to release glutathione.

* * * * *

UNITED STATES PATENT AND TRADEMARK OFFICE
CERTIFICATE OF CORRECTION

PATENT NO. : 3,961,959
DATED : June 8, 1976
INVENTOR(S) : MITSUTO FUJIWHARA et al It is certified that error appears in the above-identified patent and that said Letters Patent are hereby corrected as shown below:

Column 1, line 52: after "sensitive", delete "to".

Column 2, line 21: after "is not", delete the comma (",").

Column 2, line 52: replace "piperidone" with ---pyrrolidone---.

Column 6, line 39: replace "mercaptotrazole" with ---mercaptotetrazole---.

Column 6, line 47: replace "Exemplary" with ---Elementary---.

Column 8, line 32: before "molar" (first occurrence), insert ---two---.

Column 9, line 4: replace "sensitve" with ---sensitive---.

Column 9, line 14: replace "cooperatively" with ---comparatively---.

Column 9, line 64: before "more", replace "with" with ---of---.

Column 9, last line: replace "different" with ---diffusion---.

Column 10, line 32: rewrite "non coupler" as --non-coupler--.

UNITED STATES PATENT AND TRADEMARK OFFICE
CERTIFICATE OF CORRECTION

PATENT NO. : 3,961,959
DATED : June 8, 1976
INVENTOR(S) : MITSUTO FUJIWHARA et al It is certified that error appears in the above-identified patent and that said Letters Patent are hereby corrected as shown below:

Column 10, line 42: replace "affect" with ---effect---.

Column 11, lines 9, 27 and 39: replace "to 11" with ---to 1 ℓ.---.

Column 12, line 6: before "alkali", replace "an" with ---and---.

Column 12, line 48: replace "to 11" with ---to 1 ℓ.---.

Column 13, line 24: replace "shown" with ---show---.

Column 13, line 38: before "15 ml.", replace "is" with ---in---.

Column 13, line 40: before "triacetate", insert ---a---.

Column 14, line 9: before "solution", insert ---This--- and begin a new paragraph.

Column 14, line 14: replace "sitrring" with ---stirring---.

Column 14, line 45: replace "to 11" with ---to 1 ℓ.---.

Column 14, line 66: replace "butylphenoxyl" with ---butylphenoxy---.

UNITED STATES PATENT AND TRADEMARK OFFICE
CERTIFICATE OF CORRECTION

PATENT NO. : 3,961,959
DATED : June 8, 1976
INVENTOR(S) : MITSUTO FUJIWHARA et al It is certified that error appears in the above-identified patent and that said Letters Patent are hereby corrected as shown below:

Column 15, lines 41 and 67: replace "to 11" with
---to 1 ℓ.---.

Column 16, Claim 1, line 2: replace "protographic" with
---photographic---.

Column 20, Claim 20, line 4: replace "hterocyclic" with
---heterocyclic---.

UNITED STATES PATENT AND TRADEMARK OFFICE
CERTIFICATE OF CORRECTION

PATENT NO. : 3,961,959
DATED : June 8, 1976
INVENTOR(S) : MITSUTO FUJIWHARA et al It is certified that error appears in the above–identified patent and that said Letters Patent are hereby corrected as shown below:

Column 16, line 24, in Claim 1: before "selected", insert the following language:

--- of non-metallic atoms forming a heterocyclic ring ---.

Signed and Sealed this

Twenty-fourth Day of August 1976

[SEAL]

Attest:

RUTH C. MASON
Attesting Officer

C. MARSHALL DANN
Commissioner of Patents and Trademarks